United States Patent [19]

Surabian

[11] Plant 4,140

[45] Nov. 1, 1977

[54] PLUM TREE

[76] Inventor: Dennis Surabian, P.O. Box 206, Reedley, Calif. 93654

[21] Appl. No.: 755,354

[22] Filed: Dec. 29, 1976

[51] Int. Cl. ..... A01H 5/03

[52] U.S. Cl. ..... Plt./38

[58] Field of Search ..... Plt./38

*Primary Examiner*—Robert E. Bagwill

*Attorney, Agent, or Firm*—Huebner & Worrel

[57] ABSTRACT

A plum tree generally, similar to the Laroda plum tree (unpatented), which bears yellow fleshed, freestone fruit having a skin coloration which appears earlier and is much darker when ripe than that of the Laroda.

1 Drawing Figure

BACKGROUND OF THE VARIETY

The present invention relates to a new and distinct variety of plum tree which is generally similar in tree and fruit to the Laroda Plum Tree (unpatented) variety from which it was obtained by open pollination and which bears fruit which matures at approximately the same time, but which is much darker when ripe, and in which the change to the color of ripeness begins much earlier than in the Laroda variety.

The Laroda Plum Tree bears large, deep reddish-purple skinned fruit which reaches shipping maturity before it ripens on the tree and which has excellent market acceptance. Since most fruits rely on eye appeal for their sales, it is desirable that they reach final coloration as early as possible to provide a sales advantage similar to that provided by a similar fruit which ripens at an earlier date. The ideal in this respect, of course, would be a fruit which has a pleasing final coloration which is reached comparatively early in its development.

ORIGIN AND ASEXUAL REPRODUCTION OF THE NEW VARIETY

My new variety of plum tree was discovered as a seedling by me in 1970 as one of 36 open pollinated seedlings from a Laroda (unpatented) plum tree which I grew on a ranch owned by me located at 8743 East Alta Ave. near the City of Reedley, in the County of Fresno, in the State of California. The present variety was asexually reproduced by me by grafting onto several host trees located on a ranch which I farm and of which I own an undivided interest at 7669 South Frankwood Ave., near the City of Reedley, in the County of Fresno, in the State of California. The fruit and tree characteristics resulting from such grafting proved identical to those of the originally selected seedling.

SUMMARY OF THE NEW VARIETY

The instant variety of plum is characterized by perpetuating the general characteristics of the Laroda Plum Tree but has the important distinction of bearing fruit which develops its final coloration earlier than does that borne by the Laroda variety, and which has a much darker coloration when said coloration is fully developed. The new plum tree is of vigorous growth bearing freestone, globose fruit having blue-violet, almost black, skin coloration and having yellow, firm-textured flesh which assumes a brilliant red coloration in storage.

BRIEF DESCRIPTION OF THE DRAWING

The accompanying drawing is a color photograph of four mature fruits of the subject variety, with two of the fruits divided on the suture plane to show the flesh color and the stone, together with a representative twig showing characteristic leaves.

DETAILED DESCRIPTION

Referring more specifically to the pomological details of this new and distinct variety of plum tree, the following has been observed under the ecological conditions prevailing in the designated orchard near Reedley, Calif. All major color code plate identifications are by reference to the Nickerson Color Fan of the American Horticultural Council.

TREE

Size: Medium.

Vigor: Vigorous.

Figure: Controlled by pruning.

Regularity of Bearing: Regular.

Leaves:

- *Size.*—Large.
- *Length.*—90 mm.
- *Width.*—40 mm.
- *Shape.*—Elliptic, apex accuminate.
- *Color.*—Upperside moderate olive green (7.5 GY 4/4), underside moderate olive green (2.5 GY 4/3).
- *Marginal form.*—Serrate.
- *Petiole.*—Length 10 mm., thickness 1½ mm.
- *Glandular characteristics.*—None to two, usually two at base of leaf, reniform.
- *Stipules.*—Resemble the leaves, but very narrow, length 10 mm.

Flowers:

- *Date of bloom.*—March 1 to March 10.
- *Size.*—Average.
- *Color.*—White.

FRUIT

Maturity: With Laroda, July 10 to July 25.

Size:

- *Uniformity.*—Varies in size.
- *Axial diameter.*—50 mm. average.
- *Transverse in suture plane.*—55 mm. average.
- *Transverse at right angles to suture plane.*—52 mm. average.

Form: Globose, symetrical.

- *Suture.*—Very shallow but distinct, from apex into stem cavity.
- *Ventral surface.*—Rounded, lips equal.

*Stem cavity.*—Elongated toward suture, width 18 mm., length 20 mm., depth 9 mm.

*Apex.*—Flattened.

*Pistil point.*—None, pistil location just distinguishable.

Skin:

*Thickness.*—Normal.

*Tendency to crack.*—None.

*Color.*—Very deep blue-violet, essentially black.

*Pubescence.*—None.

Flesh:

*Color.*—When ripe deep yellow (2.5 Y 6/8) at skin to white at pit cavity, after two months in storage becomes brilliant red.

*Color of pit cavity.*—White to brilliant yellow (2.5 Y 9/9).

*Juice.*—Abundant.

*Flavor.*—Good, fully developed when permitted to ripen on tree or after removal from refrigeration for several days.

*Aroma.*—Mild.

*Texture.*—Firm.

*Ripening.*—Even.

Stone:

*Type.*—Freestone.

*Size.*—Smaller than Laroda, length 20 mm., width 20 mm.

*Form.*—Almost circular viewed at right angles to suture, slight point at apex.

*Surface.*—Smooth without cavities.

*Sides.*—Dorsal narrow groove from base three-fourths of the way to apex, ventral narrow, wing at center, grooves shallow to almost missing.

*Color.*—Light orange (5 YR 8/7).

Use: Fresh.

Keeping quality: Excellent.

Shipping quality: Excellent.

Although the new variety of plum tree possesses the described characteristics as a result of the growing conditions in Fresno County, Calif., in the central portion of the San Joaquin Valley, it is to be understood that variations of the usual magnitude in characteristics incident to growing conditions, fertilization, pruning and pest control are to be expected.

Having thus described and illustrated my new variety of plum tree, what is new and desired to be secured by Letters Patent is:

1. A new and distinct variety of plum tree, substantially as illustrated and described, characterized by its vigorous growth and regular bearing of large, yellow fleshed when ripe, freestone fruit whose flesh becomes brilliantly red in storage; and by its general resemblance to the Laroda (unpatented) plum tree from which it is distinguished by its earlier appearing final skin coloration and from which it is further distinguished by such coloration being much darker, almost black.

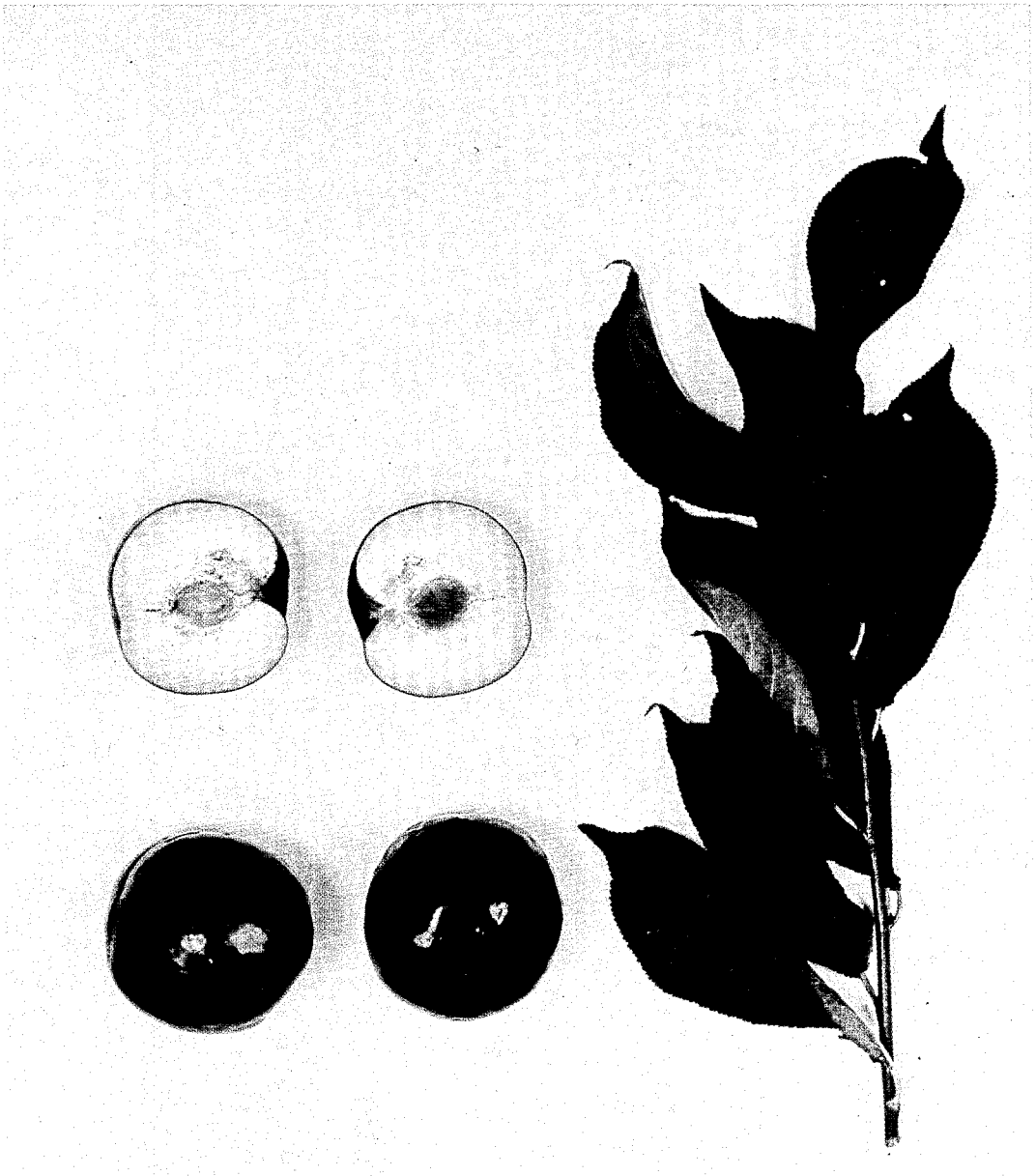

* * * * *